United States Patent [19]

Baker et al.

[11] Patent Number: 5,696,284

[45] Date of Patent: Dec. 9, 1997

[54] PROCESS FOR THE CARBONYLATION OF ALKYL ALCOHOLS AND/OR REACTIVE DERIVATIVES THEREOF

[75] Inventors: Michael James Baker, Hull, England; Carl Sherman Garland, Silver Spring, Md.; Martin Francis Giles, Ashford; Georgios Rafeletos, Canterbury, both of England

[73] Assignee: BP Chemicals Limited, London, England

[21] Appl. No.: 596,488

[22] Filed: Feb. 5, 1996

[30] Foreign Application Priority Data

| Jun. 21, 1995 | [GB] | United Kingdom | 9512606 |
| Jul. 19, 1995 | [GB] | United Kingdom | 9514745 |
| Oct. 6, 1995 | [GB] | United Kingdom | 9520441 |
| Nov. 23, 1995 | [GB] | United Kingdom | 9524037 |

[51] Int. Cl.⁶ ............................ C07C 67/36; C07C 51/12
[52] U.S. Cl. ............................................ 560/232; 562/519
[58] Field of Search ............................ 560/232; 562/519

[56] References Cited

U.S. PATENT DOCUMENTS

| 3,772,380 | 11/1973 | Paulik et al. | 260/488 K |
| 4,096,164 | 6/1978 | Ellgen et al. | 260/449 R |
| 4,358,411 | 11/1982 | Porcelli et al. | 260/546 |
| 5,510,524 | 4/1996 | Garland et al. | 562/519 |

FOREIGN PATENT DOCUMENTS

| 0031606 | 7/1981 | European Pat. Off. |
| 0616997 | 9/1994 | European Pat. Off. |
| 0618183 | 10/1994 | European Pat. Off. |
| 0618184 | 10/1994 | European Pat. Off. |
| 0 643 034 A1 | 3/1995 | European Pat. Off. |
| 0643034 | 3/1995 | European Pat. Off. |
| 2317269 | 2/1977 | France. |
| 1767150 | 5/1972 | Germany. |
| 1234641 | 6/1971 | United Kingdom. |
| 1234642 | 6/1971 | United Kingdom. |
| 1276326 | 6/1972 | United Kingdom. |
| 2146637 | 4/1985 | United Kingdom. |
| 9611179 | 4/1996 | WIPO. |

OTHER PUBLICATIONS

Journal of Molecular Catalysts, 2(1977) 149–161 D. Brodzki, B. Denise and G. Pannetier.

J. Chem. Soc., Chem. Commun., 1995—pp. 1045–1046. Dramatic Acceleration of Migratory Insertion in [MeIr(CO)$_2$ $_3$]—by Methanol and by Tin ( ) Iodide.

*Primary Examiner*—Paul J. Killos
*Assistant Examiner*—Rosalynd A. Keys
*Attorney, Agent, or Firm*—Brooks Haidt Haffner & Delahunty

[57] ABSTRACT

In a process for the liquid phase carbonylation of an alkyl alcohol such as methanol, and/or a reactive derivative thereof to produce the corresponding carboxylic acid and/or ester, in the presence of an iridium catalyst, an alkyl halide and water, the reaction is promoted by the presence of at least one promoter selected from cadmium, mercury, zinc, gallium, indium and tungsten, optionally with a co-promoter selected from ruthenium, osmium and rhenium.

12 Claims, No Drawings

PROCESS FOR THE CARBONYLATION OF ALKYL ALCOHOLS AND/OR REACTIVE DERIVATIVES THEREOF

The present invention relates to a carbonylation process and in particular to a process for the carbonylation of alkyl alcohols and/or reactive derivatives thereof in the presence of an iridium catalyst.

Carbonylation processes in the presence of iridium catalysts are known and are described, for example, in U.S. Pat. No. 3,772,380, European patent publication number EP 0618184-A, UK patents GB 1276326, GB 1234641 and GB 1234642.

Carbonylation in the presence of an iridium catalyst and co-promoter selected from ruthenium and osmium is described in European patent publication number EP-0643034-A.

It has now been found that a promoter selected from the group consisting of cadmium, mercury, zinc, gallium, indium and tungsten has a beneficial effect on the rate of carbonylation of an alkyl alcohol and/or a reactive derivative thereof in the presence of an iridium catalyst.

Thus, according to the present invention there is provided a process for the production of a carboxylic acid by carbonylation of an alkyl alcohol and/or a reactive derivative thereof which process comprises contacting in a carbonylation reactor said alcohol and/or a reactive derivative thereof with carbon monoxide in a liquid reaction composition comprising: (a) an iridium catalyst, (b) an alkyl halide, (c) at least a finite concentration of water, and (d) a promoter selected from the group consisting of cadmium, mercury, zinc, gallium, indium and tungsten.

Also according to the present invention there is provided a catalyst system for the carbonylation of an alkyl alcohol and/or a reactive derivative thereof which catalyst system comprises (a) an iridium catalyst, (b) an alkyl halide and (c) a promoter selected from the group consisting of cadmium, mercury, zinc, gallium, indium and tungsten.

The promoters of the present invention are not only generally cheaper than promoters such as ruthenium and osmium, but at least cadmium, mercury, zinc, gallium and indium are believed to be less likely to form volatile species in the carbonylation reaction.

Suitable alkyl alcohols comprise $C_1$ to $C_{10}$, preferably $C_1$ to $C_6$, more preferably $C_1$ to $C_4$ alkyl alcohols and yet more preferably methanol. Preferably, the alkyl alcohol is a primary or secondary alkyl alcohol. The product of the carbonylation of an alcohol having n carbon atoms and/or a derivative thereof is a carboxylic acid having n+1 carbon atoms and/or an ester of a carboxylic acid having n+1 carbon atoms and the alcohol having n carbon atoms. Thus the product of the carbonylation of methanol and/or a derivative thereof is acetic acid and/or methyl acetate.

Suitable reactive derivatives of the alkyl alcohol include the corresponding alkyl ester of the alcohol and the corresponding carboxylic acid product, dialkyl ethers and alkyl halides, preferably iodides or bromides. Suitable reactive derivatives of methanol include methyl acetate, dimethyl ether and methyl iodide. A mixture of alkyl alcohol and reactive derivatives thereof may be used as reactants in the process of the present invention. Preferably, methanol and/or methyl acetate are used as reactants. At least some of the alkyl alcohol and/or reactive derivative thereof will be converted to, and hence present as, alkyl esters in the liquid reaction composition by reaction with carboxylic acid product or solvent. The concentration in the liquid reaction composition, of alkyl ester is suitably in the range 1 to 70% by weight, preferably 2 to 50% by weight and yet more preferably 3 to 35% by weight.

Water may be formed in situ in the liquid reaction composition, for example, by the esterification reaction between alkyl alcohol reactant and carboxylic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Suitably, the concentration of water in the liquid reaction composition is in the range 1 to 15% by weight, preferably 1 to 10% by weight, more preferably no greater than 6.55 by weight.

The iridium component of the catalyst in the liquid reaction composition may comprise any iridium containing compound which is soluble in the liquid reaction composition. The iridium component of the catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferable chloride-free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution.

Preferably, the iridium catalyst concentration in the liquid reaction composition is in the range 100 to 6000 ppm by weight of iridium.

The cadmium, mercury, zinc, gallium, indium or tungsten promoter may comprise any cadmium, mercury, zinc, gallium, indium or tungsten containing compound which is soluble in the liquid reaction composition. The promoter may be added to the liquid reaction composition for the carbonylation reaction in any suitable form which dissolves in the liquid reaction composition or is convertible to a soluble form.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used include $Hg(OAc)_2$, $HgI_2$, $HgBr_2$, $HgCl_2$, $Hg_2I_2$, and $Hg_2Cl_2$.

Examples of suitable zinc-containing compounds which may be used include $Zn(OAc)_2$, $Zn(OH)_2$, $ZnI_2$, $ZnBr_2$, $ZnCl_2$, and zinc acetylacetonate.

Examples of suitable gallium-containing compounds which may be used include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used include indium acetylacetonate, indium acetate, $InCl_3$, $InBr_3$, $InI_3$, $InI$ and $In(OH)_3$.

Examples of suitable tungsten-containing compounds which may be used include $W(CO)_6$, $WCl_4$, $WCl_6$, $WBr_5$, $WI_2$, $C_9H_{12}W(CO)_3$ and any tungsten chloro-, bromo- or iodo-carbonyl compound.

The molar ratio of each promoter: iridium catalyst is suitably in the range (0.1 to 20):1, preferably (0.5 to 10):1. More than one promoter may be used.

An optional co-promoter selected from the group consisting of ruthenium, osmium and rhenium may also be used and may comprise any ruthenium, osmium or rhenium containing compound which is soluble in the liquid reaction composition. The optional co-promoter may be added to the liquid reaction composition for the carbonylation reaction in any suitable form which dissolves in the liquid reaction composition or is convertible to a soluble form.

Examples of suitable ruthenium-containing compounds which may be used as optional co-promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis (benzene)diruthenium(II), dichloro(cycloocta-1,5-diene) ruthenium (II) polymer and tris(acetylacetonate)ruthenium (III).

Examples of suitable osmium containing compounds which may be used as optional co-promoter include osmium (III) chloride hydrate and anhydrous, osmium metal, osmium tetraoxide, triosrniumdodecacarbonyl, $[Os(CO)_4I_2]$, $[Os(CO)_3I_2]_2$, $[Os(CO)_3I_3]^-H^+$, pentachloro-μ-nitrododiosmium and mixed osmium halocarbonyls such as tricarbonyldichloroosmium (II) dimer and other organoosmium complexes.

Examples of suitable rhenium-containing compounds which may be used as optional co-promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $[Re(CO)_4I_2]^-H^+$ and $ReCl_5.yH_2O$.

The molar ratio of each optional co-promoter: iridium catalyst is suitably in the range (0.1 to 20):1, preferably (0.5 to 10):1.

Preferably, the iridium, promoter and optional co-promoter containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse affect on the reaction rate may be minimised by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a corrosion metal removal process is described in U.S. Pat. No. 4,007,130. Preferably, ionic contaminants are kept below a concentration at which they would generate 500 ppm $I^-$, preferably less than 250 ppm $I^-$ in the liquid reaction composition.

Suitable alkyl halides have alkyl moieties corresponding to the alkyl moiety of the alkyl alcohol reactant and are preferably $C_1$ to $C_{10}$, more preferably $C_1$ to $C_6$ and yet more preferably $C_1$ to $C_4$ alkyl halides. Preferably the alkyl halide is an iodide or bromide, more preferably an iodide. A preferred alkyl halide is methyl iodide. Preferably, the concentration of alkyl halide in the liquid reaction composition is in the range 1 to 20%, preferabiy 2 to 16% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the reaction is suitably in the range 1 to 70 bar, preferably 1 to 35 bar, more preferably 1 to 15 bar.

The total pressure of the carbonylation reaction is suitably in the range 10 to 200 barg, preferably 10 to 100 barg, more preferably 15 to 50 barg. The temperature of the carbonylation reaction is suitably in the range 100° to 300° C., preferably in the range 150° to 220° C.

Carboxylic acid and/or ester thereof may be used as a solvent for the reaction.

The process of the present invention may be performed as a batch or a continuous process, preferably as a continuous process.

The carboxylic acid and/or ester thereof product may be removed from the reactor by withdrawing liquid reaction composition and separating the carboxylic acid product and/or ester therof by one or more flash and/or fractional distillation stages from the other components of the liquid reaction composition such as iridium catalyst, cadmium, mercury, zinc, gallium, indium or tungsten promoter, optional co-promoter, alkyl halide, water and unconsumed reactants which may be recycled to the reactor to maintain their concentrations in the liquid reaction composition. The carboxylic acid product and/or ester thereof may also be removed as a vapour from the reactor.

The invention will now be illustrated by way of example only by reference to the following examples.

Cadmium, mercury and zinc promoters

A 150 cm³ Hastelloy B2 (Trade Mark) autoclave equipped with a Magnedrive (Trade Mark) stirrer, liquid injection facility and cooling coils was used for a series of batch carbonylation experiments. A gas supply to the autoclave was provided from a ballast vessel, feed gas being provided to maintain the autoclave at a constant pressure. The rate of gas uptake at a certain point in a experiment was used to calculate the carbonylation rate, as number of moles of reactant consumed per liter of cold degassed reactor composition per hour (mol/l/hr), at a particular reactor composition (reactor composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace. The data are reported at calculated methyl acetate concentrations of 26%, 15% and 6% which correspond to typical standing concentrations in the liquid reaction composition in a continuous process. For 15% calculated methyl acetate concentration in such a continuous process the concentration of other components of such a liquid reaction composition are: methyl iodide about 5 to 8%, typically about 5 to 6%, water about 6 to 8% and acetic acid balance.

For each batch carbonylation experiment the autoclave was charged with cadmium, mercury or zinc promoter, optional co-promoter and the liquid components of the liquid reaction composition excluding part of the water charge (6.5 g), in which the iridium catalyst was dissolved (see Table 1).

The autoclave was flushed twice with nitrogen and once with carbon monoxide (being pressurised with each gas to approximately 25 barg) and was then heated, by means of electrical heating coils, to a temperature of 190° C. under 1 bara pressure of carbon monoxide. A rapid and consistent rate of stirring (1000 rpm) was employed. Once stable at temperature the aqueous iridium catalyst solution was injected into the autoclave. Simultaneously, the autoclave was pressurised to 22 barg with carbon monoxide fed from the ballast vessel. The pressure in the autoclave was subsequently maintained at approximately 22 barg (see Table 2) with carbon monoxide fed from the ballast vessel. The partial pressure of carbon monoxide was not measured but was believed to be less than 15 bar. The reaction temperature was maintained within ±1° C. of the desired reaction temperature (190° C.).

Gas uptake from the ballast vessel was measured throughout the course of the experiment and used to calculate carbonylation rate. After uptake of carbon monoxide from the ballast vessel has ceased the autoclave was isolated from the gas supply and was cooled to room temperature by means of the cooling coils. The autoclave Was vented and samples of the liquid reaction composition and gases in the headspace of the autoclave were analysed by gas chromatography. The major product in each batch carbonylation experiment according to the present invention was acetic acid. By-product yields are collated in Table 2.

Examples 1–10 and Experiments A–I

The results given in Table 2 show that cadmium does not act as a carbonylation catalyst under the reaction conditions (Experiment D). The results in Table 2 also show that cadmium promotes iridium catalysed methanol carbonylation (compare Examples 1–3 with Experiments A–D). The results in Table 2 show that the carbonylation rate increases as the cadmium concentration increases. The results in Table 2 show that mercury and zinc are also promoters for iridium catalysed carbonylation of methanol (Examples 4–7), but are not as effective as cadmium.

The results in Table 2 also show that cadmium and zinc promote an iridium/ruthenium carbonylation of methanol; (Experiment E compared with Examples 8, 9 and 10).

No evidence of precipitation was observed in Examples 1 to 7 which indicates that cadmium, mercury and zinc are soluble.

TABLE 1

Autoclave Charges

| Experiment | Catalyst System (molar ratio) | Catalyst $IrCl_3 \cdot 3H_2O$ (g) | Optional Co-Promoter $Ru_3(CO)_{12}$ (g) | Promoter | Amount of Promoter (g) | Methyl Acetate (g) | Water (g) | Methyl iodide (g) | Acetic Acid (g) |
|---|---|---|---|---|---|---|---|---|---|
| Experiment A | Ir | 0.331 | — | — | — | 28.80 | 10.20 | 5.35 | 45.34 |
| Experiment B | Ir | 0.331 | — | — | — | 28.80 | 10.15 | 5.31 | 45.32 |
| Experiment C | Ir | 0.331 | — | — | — | 28.80 | 10.17 | 6.67 | 44.00 |
| Experiment D | Cd (2) | — | — | $CdI_2$ | 0.680 | 28.80 | 10.24 | 4.81 | 45.46 |
| Example 1 | Ir/Cd (1:2) | 0.331 | — | $CdI_2$ | 0.680 | 28.81 | 10.20 | 5.34 | 44.66 |
| Example 2 | Ir/Cd (1:5) | 0.331 | — | $CdI_2$ | 1.710 | 28.80 | 10.17 | 5.33 | 43.68 |
| Example 3 | Ir/Cd (4:10) | 0.331 | — | $CdI_2$ | 3.430 | 28.80 | 10.18 | 5.44 | 41.92 |
| Example 4 | Ir/Hg (1:5) | 0.331 | — | $HgI_2$ | 2.130 | 28.80 | 10.16 | 5.33 | 43.21 |
| Example 5 | Ir/Hg (1:5) | 0.331 | — | $Hg(OAc)_2$ | 1.490 | 28.80 | 10.18 | 6.65 | 42.57 |
| Example 6 | Ir/Zn (1:5) | 0.331 | — | $ZnI_2$ | 1.490 | 28.80 | 10.16 | 5.35 | 43.84 |
| Example 7 | Ir/Zn (1:5) | 0.331 | — | $ZnCl_2$ | 0.633 | 28.81 | 10.17 | 6.65 | 43.36 |
| Experiment E | Ir/Ru (1:2) | 0.332 | 0.401 | — | — | 28.81 | 10.18 | 5.87 | 44.42 |
| Experiment F | Ir/Ru (1:5) | 0.331 | 0.995 | — | — | 28.81 | 10.17 | 6.70 | 43.04 |
| Experiment G | Ir/Re (1:5) | 0.334 | 1.535 g $Re_2(CO)_{10}$ | — | — | 28.80 | 10.16 | 7.31 | 41.85 |
| Experiment H | Ir/Ru/Os (1:2:2) | 0.331 | 0.401 and 0.56 g $Os_3(CO)_{12}$ | — | — | 28.82 | 10.18 | 6.38 | 43.31 |
| Experiment I | Ir/Ru/Re (1:2:2) | 0.332 | 0.400 and 0.613 g $Re_2(CO)_{10}$ | — | — | 28.80 | 10.19 | 6.69 | 43.60 |
| Example 8 | Ir/Ru/Cd (1:2:2) | 0.331 | 0.400 | $CdI_2$ | 0.679 | 28.80 | 10.17 | 5.83 | 43.75 |
| Example 9 | Ir/Ru/Cd (1:2:2) | 0.332 | 0.401 | $CdI_2$ | 0.682 | 28.82 | 10.17 | 5.86 | 43.73 |
| Example 10 | Ir/Ru/Zn (1:2:2) | 0.331 | 0.401 | $ZnCl_2$ | 0.256 | 28381 | 10.17 | 6.39 | 43.63 |

TABLE 2

Rate, Stability and By-product Data

| Run | Reactor Pressure at 15 wt % Methyl acetate[c] | Rate at 26, 15 and 6% wt % MeOAc concentration[c] (Mol/l/hr) | | | [Ethyl Iodide] (ppm) | [Ethyl Acetate] (ppm) | [Propionic Acid] (ppm) | Methane[a] | Carbon Dioxide[a] | Appearance of Reaction Composition at End of Experiment |
|---|---|---|---|---|---|---|---|---|---|---|
| Experiment A | 22.4 | 11.1 | 9.0 | 4.2 | 456 | 233 | 84 | 12.5 | 11.3 | Orange solution |
| Experiment B | 22.6 | 9.9 | 8.1 | 3.8 | 201 | 216 | 141 | 10.7 | 5.8 | Orange solution |

TABLE 2-continued

Rate, Stability and By-product Data

| Run | Reactor Pressure at 15 wt % Methyl acetate[c] | Rate at 26, 15 and 6% wt % MeOAc concentration[c] (Mol/l/hr) | | | [Ethyl Iodide] (ppm) | [Ethyl Acetate] (ppm) | [Propionic Acid] (ppm) | Methane[a] | Carbon Dioxide[a] | Appearance of Reaction Composition at End of Experiment |
|---|---|---|---|---|---|---|---|---|---|---|
| Experiment C | 22.8 | 9.9 | 8.3 | 4.4 | | | | | | Orange solution |
| Experiment D | (23.7)[b] | | 0.0 | | <2 | 65 | 55 | 2.0 | 0.9 | Off-white solution |
| Example 1 | 22.6 | 14.5 | 13.3 | 7.5 | 661 | 306 | 115 | 15.5 | 9.9 | Orange solution |
| Example 2 | 22.6 | 18.4 | 16.3 | 11.3 | 653 | 236 | 118 | 17.0 | 20.4 | Orange solution |
| Example 3 | 22.5 | 19.2 | 17.6 | 11.9 | 626 | 155 | 122 | 16.7 | 35.5 | Brown-green solution |
| Example 4 | 22.6 | 13.7 | 12.4 | 5.7 | 495 | 232 | 115 | 33.7 | 37.8 | Orange solution |
| Example 5 | 22.8 | 13.1 | 11.8 | 6.2 | 305 | 237 | 120 | 38.0 | 38.7 | Orange solution |
| Example 6 | 22.8 | 12.2 | 11.2 | 6.1 | 538 | 302 | 146 | 18.7 | 10.9 | Orange solution |
| Example 7 | 22.9 | 11.1 | 10.5 | 5.6 | 369 | 289 | 103 | 17.4 | 8.5 | Dark orange-brown solution |
| Experiment E | 22.3 | 15.1 | 13.9 | 9.8 | 389 | 211 | 69 | 11.2 | 3.3 | Orange solution |
| Experiment F | 22.5 | 19.1 | 17.4 | 11.9 | 483 | 149 | 115 | 15.3 | 5.8 | Orange precipitate in orange solution |
| Experiment G | 22.8 | 13.2 | 11.0 | 4.7 | 373 | 219 | 109 | 11.8 | 6.7 | Orange solution |
| Experiment H | 22.9 | 19.2 | 18.1 | 13.0 | 464 | 224 | 75 | 14.6 | 9.4 | |
| Experiment I | 22.8 | 17.4 | 16.3 | 9.4 | 482 | 198 | 75 | 11.6 | 3.8 | |
| Example 8 | 22.5 | 18.1 | 16.5 | 11.6 | 696 | 248 | 116 | 15.3 | 7.4 | Orange solution + cloudy orange precipitate |
| Example 9 | 22.7 | 18.7 | 17.0 | 11.1 | 696 | 246 | 118 | 16.0 | 7.0 | Orange solution + cloudy orange precipitate |
| Example 10 | 22.9 | 16.2 | 15.5 | 10.7 | 590 | 233 | 114 | 12.9 | 6.4 | |

[a] % by volume of the measured gases (CO, $CH_4$ and $CO_2$); the balance being carbon monoxide
[b] No carbonylation occurred - reactor pressure was therefore not measured at 15 wt % methyl acetate concentration
[c] Calculated concentration of methyl acetate 26%, 15% and 6% by weight-corresponding water concentrations 9.7%, 7.0% and 4.6% respectively. Methyl iodide about 5 to 8%, typically about 5 to 6%. Rate error estimated at ± 10%. MeOAc = methyl acetate Gallium and iridium promoters. Examples 11–14

The same procedure and apparatus as for the cadmium, mercury and zinc promoters was followed. The autoclave charges are given in Table 3 and the results in Table 4 for Examples 11–14. The major product in each batch carbonylation experiment according to the present invention was acetic acid.

The results given in Table 4 show that gallium and indium both promote iridium catalysed methanol carbonylation (compare Examples 11–12 with Experiments A–C).

The results in Table 4 also show that gallium and indium promote iridium/ruthenium carbonylation of methanol; (Experiment E compared with Examples 13–14).

No evidence of precipitation was observed in Examples 11 and 12 which indicates that gallium and indium are soluble.

TABLE 3

Autoclave Charges

| Experiment | Catalyst System (molar ratio) | Catalyst $IrCl_3.3H_2O$ (g) | Optional Co-Promoter $Ru_3(CO)_{12}$ (g) | Promoter | Amount of Promoter (g) | Methyl Acetate (g) | Water (g) | Methyl iodide (g) | Acetic Acid (g) |
|---|---|---|---|---|---|---|---|---|---|
| Experiment A | Ir | 0.331 | — | — | — | 28.80 | 10.20 | 5.35 | 45.34 |
| Experiment B | Ir | 0.331 | — | — | — | 28.80 | 10.15 | 5.31 | 45.32 |
| Experiment C | Ir | 0.331 | — | — | — | 28.80 | 10.17 | 6;67 | 44.00 |
| Example 11 | Ir/Ga (1:5) | 0.330 | — | $GaI_3$ | 2.105 | 28.80 | 10.17 | 5.33 | 43.23 |
| Example 12 | Ir/In (1:5) | 0.331 | — | $InI_3$ | 2.395 | 28.80 | 10.18 | 5.38 | 43.02 |
| Experiment E | Ir/Ru (1:2) | 0.332 | 0.401 | — | — | 28.81 | 10.18 | 5.87 | 44.42 |
| Example 13 | Ir/Ru/Ga (1:2:2) | 0.331 | 0.400 | $GaI_3$ | 0.848 | 28.81 | 10.16 | 5.85 | 43.59 |
| Example 14 | Ir/Ru/In (1:2:2) | 0.331 | 0.400 | $InI_3$ | 0.926 | 28.82 | 10.17 | 5.88 | 43.49 |

TABLE 4

Rate, Stability and By-product Data

| Experiment | Reactor Pressure at 15 wt % MeOAc concentration[b] | Rate at 26, 15 and 6% wt % MeOAc concentration[b] (Mol/l/hr) | | | Liquid by-products | | | Gaseous by-products | | Appearance of Reaction Composition at End of Experiment |
|---|---|---|---|---|---|---|---|---|---|---|
| | | | | | [Ethyl Iodide] (ppm) | [Ethyl Acetate] (ppm) | [Propionic Acid] (ppm) | Methane[a] | Carbon Dioxide[a] | |
| Experiment A | 22.4 | 11.1 | 9.0 | 4.2 | 456 | 233 | 84 | 12.5 | 11.3 | Orange solution |
| Experiment B | 22.6 | 9.9 | 8.1 | 3.8 | 201 | 216 | 141 | 10.7 | 5.8 | Orange solution |
| Experiment C | 22.8 | 9.9 | 8.3 | 4.4 | — | — | — | — | — | Orange solution |
| Example 11 | 22.6 | 13.4 | 11.3 | 5.7 | 497 | 255 | 143 | 17.3 | 19.3 | Orange solution |
| Example 12 | 22.8 | 16.5 | 13.9 | 8.0 | 812 | 316 | 153 | 18.9 | 24.5 | Orange solution |
| Experiment E | 22.3 | 15.1 | 13.9 | 9.8 | 389 | 211 | 69 | 11.2 | 3.3 | Orange solution |
| Example 13 | 22.5 | 19.7 | 16.6 | 9.4 | 547 | 161 | 144 | 12.0 | 7.4 | Orange solution |
| Example 14 | 22.4 | 19.1 | 7.3 | 12.7 | 682 | 179 | 115 | 12.7 | 6.1 | Orange solution with cloudy suspension |

[a]% by volume of the measured gases (CO, $CH_4$ and $CO_2$); the balance being carbon monoxide
[b]Calculated concentration of methyl acetate at 26%, 15% and 6% by weight, corresponding water concentrations 9.7%, 7% and 4.6% respectively. Methyl iodide about 5 to 8%, typically about 5 to.6%. Rate error estimated ± 10%. MeOAc = methyl acetate.

Tungsten promoter

A 300 $cm^3$ Hastelloy B2 (Trade Mark) autoclave equipped with a Dispersimax (Trade Mark) stirrer, liquid injection facility and cooling coils was used for a series of batch carbonylation experiments. A gas supply to the autoclave was provided from a ballast vessel, feed gas being provided to maintain the autoclave at a constant pressure. The rate of gas uptake at a certain point in a experiment was used to calculate the carbonylation rate, as number of moles of reactant consumed per liter of cold degassed reactor composition per hour (mol/l/hr), at a particular reactor composition (reactor composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace. The data are reported at a calculated methyl acetate concentration of 26, 15 and 6% which corresponds to a typical standing concentration in the liquid reaction composition in a continuous process. For a calculated concentration of methyl acetate of 15% the concentration of other components of such a liquid reaction composition are: methyl iodide about 5 to 8%, typically about 5 to 6%, water about 6 to 8% and acetic acid balance.

For each batch carbonylation experiment the autoclave was charged with tungsten promoter, optional co-promoter and the liquid components of the liquid reaction composition excluding part of the water charge (10.83 g), in which the iridium catalyst was dissolved (see Table 5).

The autoclave was flushed once with nitrogen to approximately 30 barg and twice with carbon monoxide to approximately 25 barg and was then heated, by means of electrical heating coils, to a temperature of 190° C. under 8 barg pressure of carbon monoxide. A rapid and consistent rate of stirring (1500 rpm) was employed. Once stable at temperature, the aqueous iridium catalyst solution was injected into the autoclave. Simultaneously, the autoclave was pressurised to 22 barg with carbon monoxide fed from the ballast vessel. The pressure in the autoclave was subsequently maintained at 22.0 barg with carbon monoxide fed from the ballast vessel. The partial pressure of carbon monoxide was calculated to be approximately 8 bar when the calculated methyl acetate concentration was 15% by weight. The reaction temperature was maintained within ±1° C. of the desired reaction temperature (190° C.).

Gas uptake from the ballast vessel was measured throughout the course of the experiment and used to calculate carbonylation rate. After uptake of carbon monoxide from the ballast vessel has ceased the autoclave was isolated from the gas supply and was cooled. The autoclave was vented and samples of the liquid reaction composition were analysed by gas chromatography. The major product in each batch carbonylation experiment according to the present invention was acetic acid. By-product yields are collated in Table 6.

Examples 15–21 and Experiments J–N

In Examples 15–17 additional methyl iodide (3 molar equivalents to tungsten) was added to compensate for probable loss of methyl iodide to tungsten iodocarbonyl components. Experiment M shows that simple addition of this extra methyl iodide to an un-promoted iridium reaction did not cause a significant increase in reaction rate.

The results given in Table 6 show that tungsten promotes iridium catalysed methanol carbonylation (compare Examples 15–17 with Experiments J–L).

Further Experiments

Further experiments (Experiment N and Examples 18–21) were performed using the same 300 ml autoclave apparatus as for tungsten. Examples 18 to 20 show the effect of increasing the amount of zinc promoters and Example 21 shows the effect of cadmium promoter.

TABLE 5

Autoclave Charges

| Experiment | Catalyst System (molar ratio) | Catalyst IrCl$_3$.3H$_2$O (g) | Promoter | Amount of Promoter (g) | Methyl Acetate (g) | Water (g) | Methyl iodide (g) | Acetic Acid (g) | Other Amounts(g) |
|---|---|---|---|---|---|---|---|---|---|
| Experiment J | Ir | 0.552 | — | — | 48.01 | 16.97 | 8.99 | 75.58 | |
| Experiment K | Ir | 0.552 | — | — | 48.02 | 16.97 | 8.99 | 75.58 | |
| Experiment L | Ir | 0.552 | — | — | 48.04 | 16.97 | 8.87 | 75.57 | |
| Experiment M | Ir | 0.552 | — | — | 48.01 | 16.96 | 12.19 | 72.24 | |
| Example 15 | Ir:W (1:5) | 0.552 | W(CO)$_6$ | 2.758 | 48.00 | 16.97 | 2.19 | 69.49 | |
| Example 16 | Ir:W (1:5) | 0.557 | W(CO)$_6$ | 2.755 | 48.00 | 16.95 | 12.18 | 69.49 | |
| Example 17 | Ir:W (1:5) | 0.552 | W(CO)6 | 2.757 | 48.00 | 16.96 | 12.19 | 69.50 | |
| Experiment N | Ir:Ru (1:2) | 0.552 | — | — | 48.01 | 16.99 | 9.80 | 74.02 | Ru$_3$(CO)$_{17}$ 0.667 |
| Example 18 | Ir:Zn (1:2) | 0.552 | ZnI$_2$ | 0.993 | 48.02 | 16.94 | 8.86 | 74.57 | |
| Example 19 | Ir:Zn (1:5) | 0.554 | ZnI$_2$ | 2.495 | 48.00 | 16.94 | 8.86 | 73.07 | |
| Example 20 | k:Zn (1:0) | 0.554 | ZnI$_2$ | 4.980 | 48.01 | 16.98 | 8.88 | 70.59 | |
| Example 21 | Ir:Cd (1:2) | 0.552 | CdI$_2$ | 1.140 | 48.02 | 16.95 | 8.87 | 74.42 | |

TABLE 6

Rate, By-product and Stability Data

| Experiment | Catalyst System (equivalents) | Rate at calculated 26, 15 and 6% wt % methyl acetate concentration (Mol/l/hr)* | | | By-products reaction composition at end of Experiment [Ethyl Iodide] (ppm) | [Ethyl Acetate] (ppm) | [Propionic Acid] (ppm) | Appearance of Reaction Composition at End of Experiment |
|---|---|---|---|---|---|---|---|---|
| Experiment J | Ir | 11.7 | 8.2 | 4.6 | 115 | 223 | 4 | Orange solution |
| Experiment K | Ir | 11.6 | 8.4 | 5.1 | 114 | 188 | 9 | Orange solution |
| Experiment L | Ir | 11.4 | 7.7 | 3.9 | 234 | 307 | <2 | Orange solution |
| Experiment M | Ir | 11.4 | 8.6 | 4.2 | 100 | 179 | <2 | Orange solution |
| Example 15 | Ir:W (1:5) | 13.2 | 9.6 | 4.8 | 295 | 326 | <2 | Orange solution + blue solid |
| Example 16 | Ir:W (1:5) | 12.3 | 9.9 | 4.9 | 328 | 288 | <2 | Orange solution + blue solid |
| Example 17 | Ir:W (1:5) | 13.0 | 9.9 | 4.0 | 315 | 335 | <2 | Orange solution + blue solid |
| Experiment N | Ir:Ru (1:2) | 20.6 | 15.6 | 9.0 | 405 | 253 | 19 | Orange solution |
| Example 18 | Ir:Zn (1:2) | 14.5 | 10.9 | 6.5 | 406 | 416 | 18 | Orange solution |
| Example 19 | Ir:Zn (1:5) | 15.6 | 12.8 | 8.1 | 408 | 408 | 10 | Orange solution |
| Example 20 | Ir:Zn (1:10) | 15.8 | 13.6 | 9.3 | 439 | 394 | 18 | Orange solution |
| Example 21 | Ir:Cd (1:2) | 13.5 | 12.5 | 9.5 | — | — | — | Orange solution |

*Estimated rate error ± 10% Water concentrations 9.7%, 7.0% and 4.6% respectively at 26, 15 and. 6% methyl acetate; methyl iodide about 5 to 8%, typically about 5 to 6% [eg in M initial methyl iodide is about 8%]

We claim:

1. A process for the carbonylation of an alkyl alcohol and/or a reactive derivative thereof which process comprises contacting in a carbonylation reactor said alcohol and/or a reactive derivative thereof with carbon monoxide in a liquid reaction composition comprising: (a) an iridium catalyst, (b) an alkyl halide, (c) at least a finite concentration of water, and (d) a promoter selected from the group consisting of cadmium, mercury, zinc, gallium, indium and tungsten.

2. A process as claimed in claim 1 in which the molar ratio of each promoter: iridium catalyst is (0.1 to 20):1.

3. A process as claimed in claim 1 in which a co-promoter selected from ruthenium, osmium and rhenium is present in the liquid reaction composition.

4. A process as claimed in claim 2 in which a co-promoter selected from ruthenium, osmium and rhenium is present in the liquid reaction composition.

5. A process as claimed in claim 4 in which the molar ratio of each co-promoter: iridium catalyst is (0.1 to 20):1.

6. A process as claimed in claim 1 in which the liquid reaction composition comprises water at a concentration in the range 1 to 15% by weight, alkyl ester at a concentration in the range 1 to 70% by weight and alkyl halide at a concentration in the range 1 to 20% by weight.

7. A process as claimed in claim 2 in which the liquid reaction composition comprises water at a concentration in the range 1 to 15% by weight, alkyl ester at a concentration in the range 1 to 70% by weight and alkyl halide at a concentration in the range 1 to 20% by weight.

8. A process as claimed in claim 5 in which the liquid reaction composition comprises water at a concentration in the range 1 to 15% by weight, alkyl ester at a concentration in the range 1 to 70% by weight and alkyl halide at a concentration in the range 1 to 20% by weight.

9. A process as claimed in claim 1 in which the partial pressure of carbon monoxide in the reactor is in the range 1 to 15 bar.

10. A process as claimed in claim 6 in which the partial pressure of carbon monoxide in the reactor is in the range 1 to 15 bar.

11. A process as claimed in claim 8 in which the partial pressure of carbon monoxide in the reactor is in the range 1 to 15 bar.

12. A process as claimed in any one of the preceding claims in which the alkyl alcohol is methanol, the alkyl halide is methyl iodide and the product of the reaction comprises acetic acid and/or methyl acetate.

* * * * *

UNITED STATES PATENT AND TRADEMARK OFFICE
CERTIFICATE OF CORRECTION

PATENT NO. : 5,696,284
DATED : December 9, 1997
INVENTOR(S) : MICHAEL JAMES BAKER ET AL It is certified that error appears in the above-indentified patent and that said Letters Patent is hereby corrected as shown below:

Column 3, line 47, "quatemise" should read --quaternise--; same column, line 54, "miniraised" should read --minimised--.

Column 5, Table 1, Experiment G, second column, "0.334" should be --0.331--; same Table, sixth column of Example 10, "28381" should be --28.81--.

Column 8, Table 3, Example 12, fourth column, "$In_3$" should be --$InI_3$--;

Column 11, Table 5, Example 20, first column, "k:Zn(1:0)" should be --Ir:Zn(1:10)--; same Table, Experiment N, last column "$Ru_3(CO)_{17}$ 0.667" should be --$Ru_3(CO)_{12}$ 0.667--.

Column 11, Table 6, Example 18, fifth column, "406" should be --400--; same Example, sixth column, "416" should be --410--.

Signed and Sealed this

Thirtieth Day of June, 1998

Attest:

BRUCE LEHMAN

Attesting Officer    Commissioner of Patents and Trademarks